US00PP12986P2

(12) United States Plant Patent
Bergman

(10) Patent No.: US PP12,986 P2
(45) Date of Patent: Sep. 17, 2002

(54) CHRYSANTHEMUM PLANT NAMED 'YELLOW YOBILLINGS'

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 18 days.

(21) Appl. No.: 09/829,491

(22) Filed: Apr. 11, 2001

(51) Int. Cl.[7] ..... A01H 5/00
(52) U.S. Cl. ..... Plt./295
(58) Field of Search ..... Plt./295

(56) References Cited

U.S. PATENT DOCUMENTS 4,616,099 A * 10/1986 Sparkes ..... 47/58

OTHER PUBLICATIONS

Shukla, et al., 1993, "Mutation studies on early and late varieties of garden chrysanthemums", J. Nuclear Agric. Biol., 22(3–4): 138–142.*

Broertjes, et al., 1980, "A mutant of a mutant of a . . . Irradiation of progressive radiation induced mutants in a mutation breeding programme with *Chrysanthumum morifolium*", Euphytica, 29: 525–530.*

Gosling, ed., 1979, "The Chrysanthemum Manual—6$^{th}$ edition", The National Chrysanthemum Society, London, Essex Telegraph Press, Ltd., pp. 329–336.*

Broertjes, et al., 1978, "Application of Mutation Breeding Methods in the Improvement of Vegetatively Propagated Crops", Elsevier Sci. Pub. Co., New York, pp. 162–175.*

Searle, et al., 1968, "Chrysanthemums The Year Round", Blanford Press, London, pp. 27–29, 320–327.*

Chan, 1966, "Chrysanthemum and rose mutations induced by X–rays", Am. Soc. Hort. Sci. Proc., pp. 613–620.*

Broertjes, 1966, Mutation breeding of chrysanthemums, Euphytica, 15: 156–162.*

Dowrick, et al. 1966, "The induction of mutations in chrysanthemum using X– and gamma radiation", Euphytica, 15: 204–210.*

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Yellow Yobillings', characterized by its uniform and upright plant habit; strong and vigorous growth habit; dark green foliage; uniform flowering response; early and freely flowering habit; large daisy-type inflorescences; bright yellow-colored ray and disc florets; and good postproduction longevity.

2 Drawing Sheets

BACKGROUND OF THE INVENTION

The present Invention relates to a new and distinct cultivar of Chrysanthemum plant, botanically known as *Chrysanthemum×morifolium* and hereinafter referred to by the name 'Yellow Yobillings'.

The new Chrysanthemum is a product of a planned breeding program conducted by the Inventor in Fort Myers, Fla. The objective of the breeding program is to create new potted Chrysanthemum cultivars that are suitable for year-round production with uniform plant growth habit, good vigor, desirable inflorescence form and floret colors, fast response time, and good postproduction longevity.

The new Chrysanthemum is a naturally-occurring whole plant mutation of a proprietary induced mutation that originated by exposing unrooted cuttings of the Chrysanthemum cultivar Yobillings, disclosed in U.S. Plant Pat. No. 11,867, to X-ray radiation in October, 1997, in Fort Myers, Fla. The new Chrysanthemum was discovered and selected by the Inventor as a single flowering plant within a population of plants of the irradiated selection in April, 1998 in Fort Myers, Fla. The selection of this plant was based on its uniform plant growth habit, good vigor, desirable inflorescence form and floret colors, fast response time, and good postproduction longevity.

Asexual reproduction of the new Chrysanthemum by vegetative tip cuttings was first conducted in Fort Myers, Fla. in July, 1998. Asexual reproduction by cuttings has shown that the unique features of this new Chrysanthemum are stable and reproduced true to type in successive generations.

SUMMARY OF THE INVENTION

The cultivar Yellow Yobillings has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yellow Yobillings'. These characteristics in combination distinguish 'Yellow Yobillings' as a new and distinct Chrysanthemum:

1. Uniform and upright plant habit.
2. Strong and vigorous growth habit.
3. Dark green foliage.
4. Uniform flowering response.
5. Can be grown as a disbud or as a spray-type.
6. Early flowering, eight-week response time.
7. Freely flowering.

8. Large daisy-type inflorescences that are about 11.3 cm in diameter.

9. Bright yellow-colored ray and disc florets.

10. Good postproduction longevity with plants maintaining good substance and color for at least three weeks in an interior environment.

Plants of the new Chrysanthemum can be compared to plants of the cultivar Yobillings. In side-by-side comparisons conducted by the Inventor in Salinas, Calif., plants of the new Chrysanthemum differ from plants of the cultivar Yobillings in the following characteristics:

1. Plants of the new Chrysanthemum are slightly less vigorous and shorter than plants of the cultivar Yobillings.

2. Plants of the new Chrysanthemum have slightly smaller inflorescences than plants of the cultivar Yobillings.

3. Plants of the new Chrysanthemum have yellow-colored ray florets whereas plants of the cultivar Yobillings have white-colored ray florets.

Plants of the new Chrysanthemum can be compared to plants of the Chrysanthemum cultivar Yellow Blush, disclosed in U.S. Plant Pat. No. 9,455. In side-by-side comparisons conducted by the Inventor in Salinas, Calif., plants of the new Chrysanthemum differ from plants of the cultivar Yellow Blush in the following characteristics:

1. Plants of the new Chrysanthemum are slightly more vigorous and stronger than plants of the cultivar Yellow Blush.

2. Plants of the new Chrysanthemum are more upright than plants of the cultivar Yellow Blush.

3. Ray florets of plants of the new Chrysanthemum are upright and slightly arching whereas ray florets of plants of the cultivar Yellow Blush are reflexed.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph on the first sheet comprises a side perspective view of a typical flowering plant of 'Yellow Yobillings' grown a disbud-type.

The photograph at the top of the second sheet comprises a close-up view of typical inflorescences of 'Yellow Yobillings' grown as a disbud-type.

The photograph at the bottom of the second sheet comprises a close-up view of typical inflorescences of the new Chrysanthemum (left) and 'Yellow Blush' (right).

DETAILED BOTANICAL DESCRIPTION

In the following description, color references are made to The Royal Horticultural Society Colour Chart except where general terms of ordinary dictionary significance are used. The following observations and measurements describe plants grown and flowered during the winter in Salinas, Calif., in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 4,000 to 6,000 foot-candles. Four unrooted cuttings were directly stuck in 15-cm containers, exposed to long day/short night conditions, and pinched once about 14 days later. At that time, the photoinductive short day/long night treatments were started. Plants used for this description were grown as disbud-types. Measurements and numerical values represent averages of typical flowering plants.

Botanical classification: *Chrysanthemum×morifolium* cultivar Yellow Yobillings.

Commercial classification: Daisy-type potted Chrysanthemum.

Parentage: Naturally-occurring whole plant mutation of a proprietary *Chrysanthemum×morifolium* induced mutation, not patented.

Propagation:

*Type.*—Terminal tip cuttings.

*Time to initiate roots.*—About four days at 21° C.

*Time to produce a rooted cutting.*—About ten days at 21° C.

*Root description.*—White, fibrous.

*Rooting habit.*—Freely branching.

Plant description:

*Appearance.*—Herbaceous daisy-type potted Chrysanthemum that can be grown as a disbud or as a spray-type. Stems mostly upright and somewhat outwardly spreading; uniform crown. Freely branching, about three lateral branches develop after removal of terminal apex (pinching); dense and full plants. Vigorous.

*Plant height.*—About 22.5 cm.

*Plant width.*—About 32 cm.

*Lateral branches.*—Length: About 17 cm. Diameter: About 4 mm. Internode length: About 1.25 cm. Strength: Strong. Texture: Pubescent. Color: 144A.

*Foliage description.*—Arrangement: Alternate. Quantity of leaves per lateral stem: About 12. Length: About 8.3 cm. Width: About 6.5 cm. Apex: Cuspidate to mucronate. Base: Attenuate to truncate. Margin: Palmately lobed, sinuses between lateral lobes divergent. Texture: Upper and lower surfaces with very fine pubescence; veins prominent on lower surface. Color: Young and fully expanded foliage, upper surface: 147A. Young and fully expanded foliage, lower surface: 147B. Venation, upper surface: 147A to 147B. Venation, lower surface: 147B. Petiole length: About 2.3 cm. Petiole diameter: About 4 mm. Petiole color: 147A to 147B.

Inflorescence description:

*Appearance.*—Daisy-type inflorescence form with elongated oblong-shaped ray florets. Inflorescences borne on terminals above foliage. Disk and ray florets arranged acropetally on a capitulum. Not fragrant. Can be grown as a disbud or as a spray-type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to two weeks of long day/short night conditions followed by photoinductive short day/long night conditions flower about 48 to 53 days later when grown during the winter.

*Postproduction longevity*.—Inflorescences maintain good color and substance for a least three weeks in an interior environment.

*Quantity of inflorescences*.—Produced as a disbud-type, all the lateral inflorescences are removed leaving only the terminal inflorescence.

*Inflorescence bud*.—Height: About 6 mm. Diameter: About 7.5 mm. Color: Close to 143A.

*Inflorescence size*.—Diameter: About 11.3 cm. Depth (height): About 2.9 cm. Diameter of disc: About 2.5 cm. Receptacle diameter: About 9 mm.

*Ray florets*.—Shape: Elongated-oblong. Orientation: Initially upright, then about 70° from vertical. Aspect: Mostly flat and slightly arched. Length: About 5.5 cm. Width: About 1.3 cm. Corolla tube length: About 6.5 mm. Apex: Acute or emarginate. Base: Attenuate; relatively short corolla tube. Margin: Entire. Texture: Smooth, glabrous, satiny. Number of ray florets per inflorescence: About 39 arranged in two or three rows. Color: When opening and fully opened, upper surface: Close to 9A. When opening and fully opened, lower surface: Close to 9C.

*Disc florets*.—Arrangement: Massed at center of receptacle. Shape: Tubular, elongated. Apex: Five-pointed. Length: About 7.5 mm. Width: Apex: About 3 mm. Base: About 1.5 mm. Number of disc florets per inflorescence: About 185. Color: Immature: Close to 144A. Mature: Apex: 9A. Mid-section: Close to 145C. Base: 155D.

*Reproductive organs*.—Androecium: Present on disc florets only. Anther color: Close to 9A to 12A. Pollen: None observed. Gynoecium: Present on both ray and disc florets.

*Seed*.—Seed production has not been observed.

Disease resistance: Resistance to pathogens common to Chrysanthemums has not been observed on plants grown under commercial greenhouse conditions.

It is claimed:

1. A new and distinct cultivar of Chrysanthemum plant named 'Yellow Yobillings', as illustrated and described.

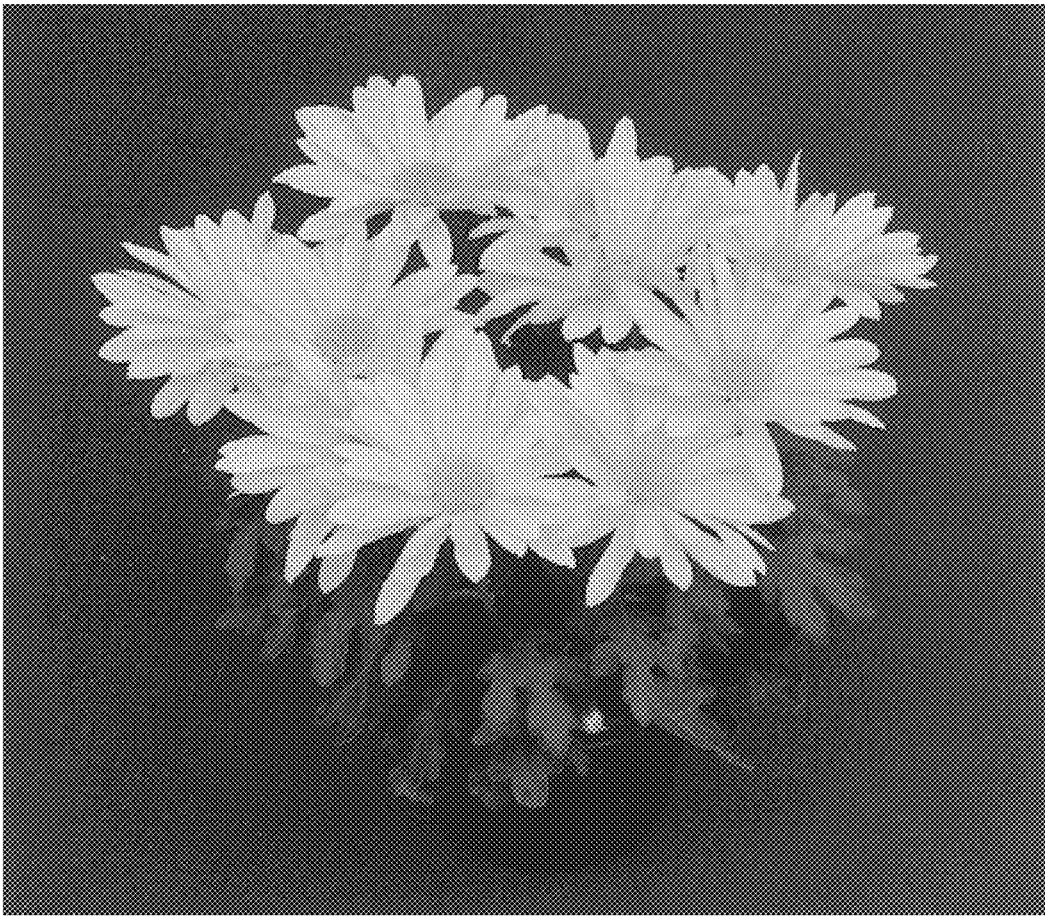

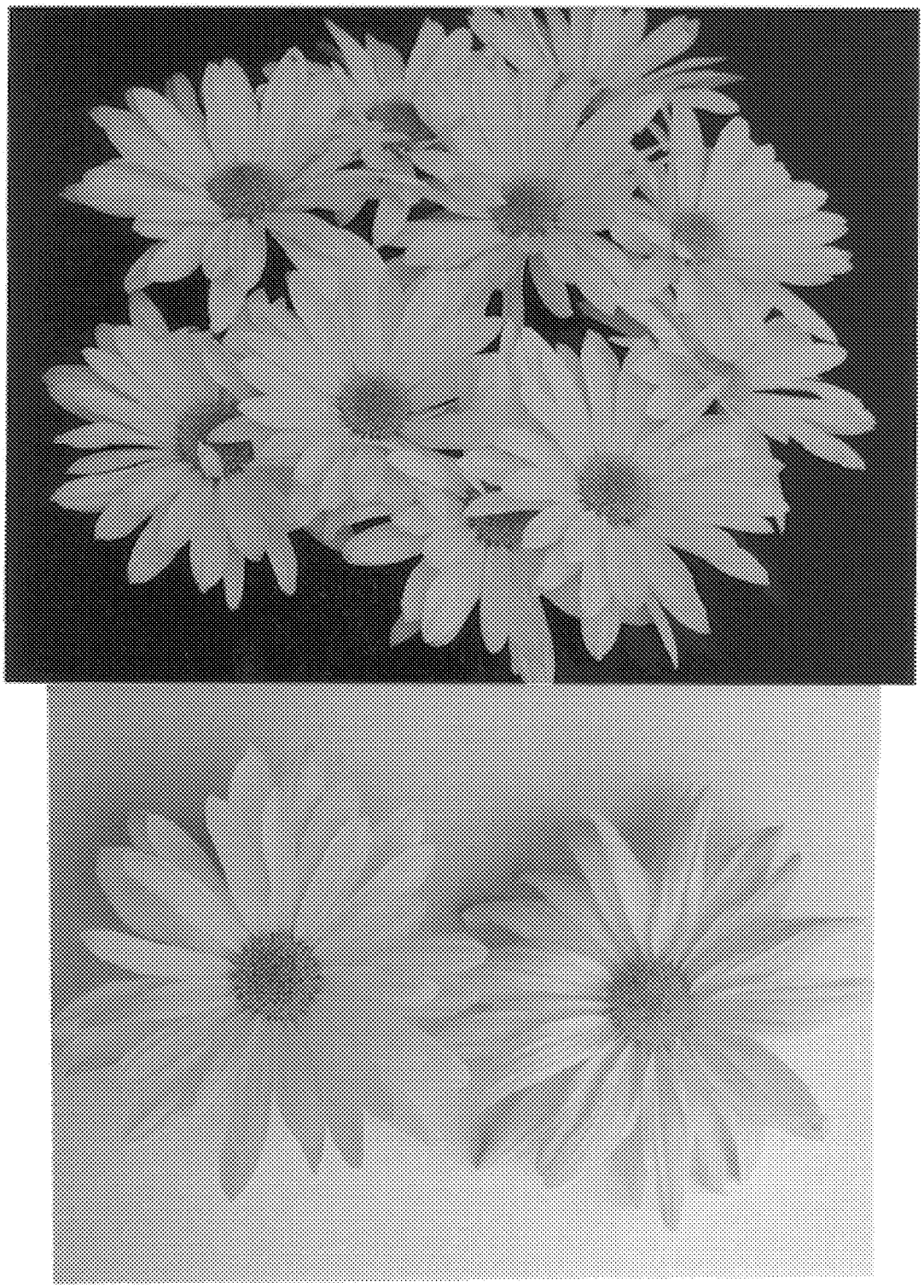

* * * * *